(12) United States Patent
Hones

(10) Patent No.: US 6,887,531 B2
(45) Date of Patent: May 3, 2005

(54) GLARE PROTECTION DEVICE

(75) Inventor: Peter Hones, Uster (CH)

(73) Assignee: Optrel AG, Wattwil (CH)

( * ) Notice: Subject to any disclaimer, the term of this patent is extended or adjusted under 35 U.S.C. 154(b) by 58 days.

(21) Appl. No.: 10/256,543

(22) Filed: Sep. 30, 2002

(65) Prior Publication Data

US 2004/0058094 A1 Mar. 25, 2004

(30) Foreign Application Priority Data

Sep. 23, 2002 (CH) .............................................. 1600/02

(51) Int. Cl.⁷ .............................. A61F 9/06; F16P 1/06
(52) U.S. Cl. ...................... 428/1.1; 428/1.31; 349/13; 349/41; 349/74; 349/104; 349/96; 359/245; 359/614; 359/352; 359/356; 359/361; 351/165; 2/432
(58) Field of Search ..................... 428/1.1, 1.3, 1.31; 349/13–14, 74, 104–106, 41, 96; 359/245, 609, 614, 352, 356, 361; 351/163, 165; 2/432

(56) References Cited

U.S. PATENT DOCUMENTS 3,382,183 A * 5/1968 Donoian et al. ............ 252/582
4,620,322 A * 11/1986 Eggenschwiler et al. .......... 2/8
4,728,173 A * 3/1988 Toth ............................. 349/14
5,239,406 A * 8/1993 Lynam ....................... 359/275
5,867,240 A * 2/1999 Crawford et al. ........... 349/118

OTHER PUBLICATIONS

Abstract, Inukai et al., JP Patent 403277676A, Dec. 9, 1991.*

* cited by examiner

Primary Examiner—Harold Pyon
Assistant Examiner—Sow-Fun Hon
(74) Attorney, Agent, or Firm—Rankin, Hill, Porter & Clark LLP

(57) ABSTRACT

The glare protection device for welding applications contains an active electro-optical filter element (2) with an electronic control circuit (3). The active filter element (2) absorbs the UV-radiation up to 380 nm. An IR-plastic filter (10) is completely joined with the active electro-optical filter element by a compact adhesive layer (11) and together with it forms a single optical and mechanical unit (1) having a high transmittance in the visual region of the spectrum. The IR-plastic filter (10) contains a dye that absorbs the infrared radiation in a wavelength range of 780–1400 nm. With this, a robust, cheap and safe in operation glare protection device for various applications is created.

16 Claims, 3 Drawing Sheets

GLARE PROTECTION DEVICE

BACKGROUND OF THE INVENTION

1. Field of the Invention

The present invention is generally related to a glare protection device and, more particularly, toward a glare protection device used as a sight window for welding protective masks, helmets, or goggles, for observing welding processes by means of automatic welding machines, or for observing glass or metal melt baths.

2. Description of Related Art

In the case of known glare protection devices of this kind, up to now glass filters with IR and UV reflecting coatings in front of the active electro-optical filter element have been used to achieve the required very high protection against UV and IR radiation. These reflecting filters, however, on the one hand, are very costly and expensive to manufacture and, on the other hand, this front-mounted glass filter is mechanically sensitive and fragile. Accordingly, under the harsh conditions of use a danger of breaking and of splintering is present. In addition to this, small holes (pinholes) in the coating are very difficult to avoid with conventional coating processes. This calls for a costly and time-intensive checking. For this reason, new solutions are sought, in order to overcome these disadvantages.

A different structure is disclosed by U.S. Pat. No. 6,021,520 with a plastic filter plate mounted in front of the active filter element, which contains dyes, in order to absorb both the UV and IR light. This proposal, however, is not suitable for more demanding applications and also is not capable of solving the task set here. The necessary thermal and mechanical stability cannot be achieved with this plastic filter plate. Also the required transparency in the visible region of the spectrum would not be given. If this filter has to absorb both UV and IR light, then in the visible region of the spectrum it would be too dark with the dyes available today to be able to carry out preparation work with protected eyes and to be able to see the welding point immediately before igniting the welding arc, which is absolutely indispensable for a glare protection device according to the invention.

The front-mounted plastic filter plate of U.S. Pat. No. 6,021,520, in principle, is interchangeable so that it may be replaced in the case of degraded characteristics, e.g., in case of distorted optics as a result of thermal-mechanical deformation. This, however, signifies an impermissible risk of handling, because there is the danger that inadvertently an interchangeable plastic filter plate would not be replaced and that thereupon in case of inadvertent use of the glare protection device without this filter serious damage to the eyes of the user could be caused, without the user being in a position to discern this in time (because UV and IR radiation are invisible).

SUMMARY OF THE INVENTION

It is, therefore, an objective of the invention presented here to overcome the disadvantages described and to create a glare protection device which is adapted for more easy and lower cost manufacture, which achieves the demanded very high absorption values, resp., low transmittance values both in the IR region and UV region of the spectrum, and which in the visible region of the spectrum nonetheless makes a high constant transparency possible. In addition to this, the high safety in use and in handling has to be assured.

In accordance with the present invention, through the splitting-up of the desired high absorption in the UV region and IR region over the two different components, namely IR plastic filter and active electro-optical filter, good optical properties are able to be achieved. By the compact interconnection of the IR plastic filter with the active filter element both the thermal-mechanical stability, the safety against splintering as well as the constancy and quality of the optical characteristics are achieved. Moreover, required high safety in use and handling are fulfilled.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
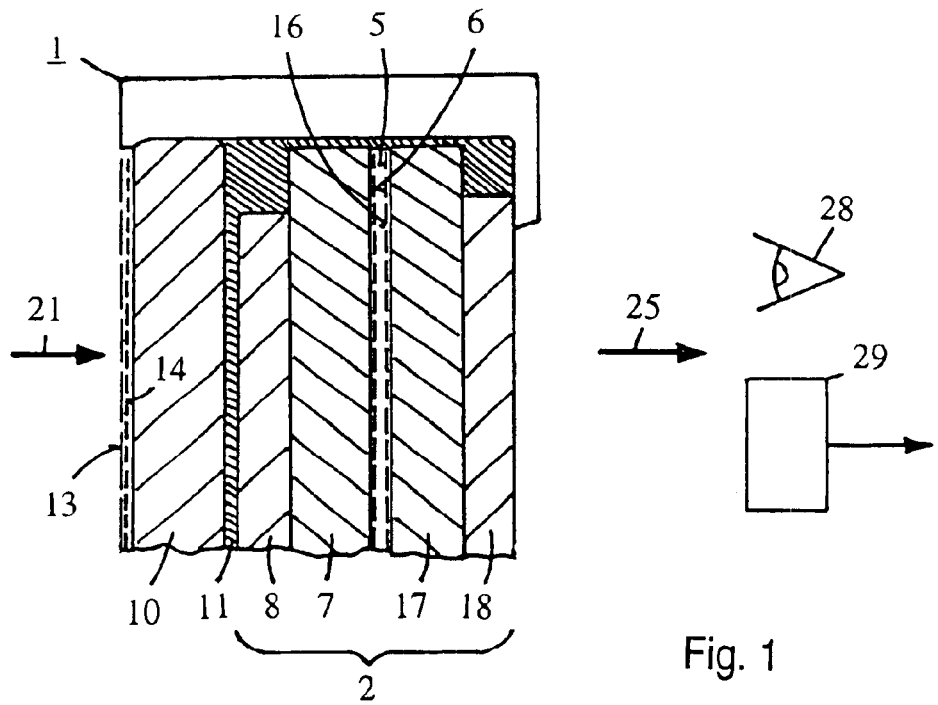
FIG. 1 illustrates construction of a glare protection device in accordance with the invention with an IR plastic filter.

FIG. 1 illustrates construction of a glare protection device 1 in accordance with the invention. The glare protection device 1 includes an active electro-optical filter element 2, which comprises one or more liquid crystal (LCD) elements with polarising layers, depending on the application, resp., according to the required maximum protection scale number, i.e., the possible darkening in the activated condition. The example of FIG. 1 illustrates an active filter element 2 with only a single LCD element, comprising an LCD layer 5 (with a layer thickness of, e.g., 4 µm) between two layers of glass 7, 17 (thickness of, e.g., 0.7 mm) with electrodes 6, 16 for driving the LCD layer and with two polarisation layers 8, 18. Stuck on to this active electro-optical filter element 2, by means of a compact layer of adhesive material 11 (adhesive material layer thickness, e.g., 50 µm), is an IR plastic filter 10. The layer thickness of the IR plastic filter amounts to, e.g., 0.7 mm and advantageously it is situated within a range of 0.5–1.5 mm. The IR plastic filter 10 is joined to the active electro-optical filter element 2 completely and free of any bubbles by the adhesive material layer 11, this in particular also in the edge zones, so that a single optical and mechanical unit is formed. With this, it is also ensured, that the IR plastic filter cannot be removed for being replaced and, therefore, that the glare protection device cannot inadvertently be utilised without an IR protection filter.

Suitable materials for the adhesive layer 11 include, for example, clear epoxy, light-hardening epoxy, and silicone resins of good optical quality. In preference, in doing so also the refraction index of the adhesive material layer is adapted to the IR plastic filter 10 and to the polarisation layer 8.

Figure 2:
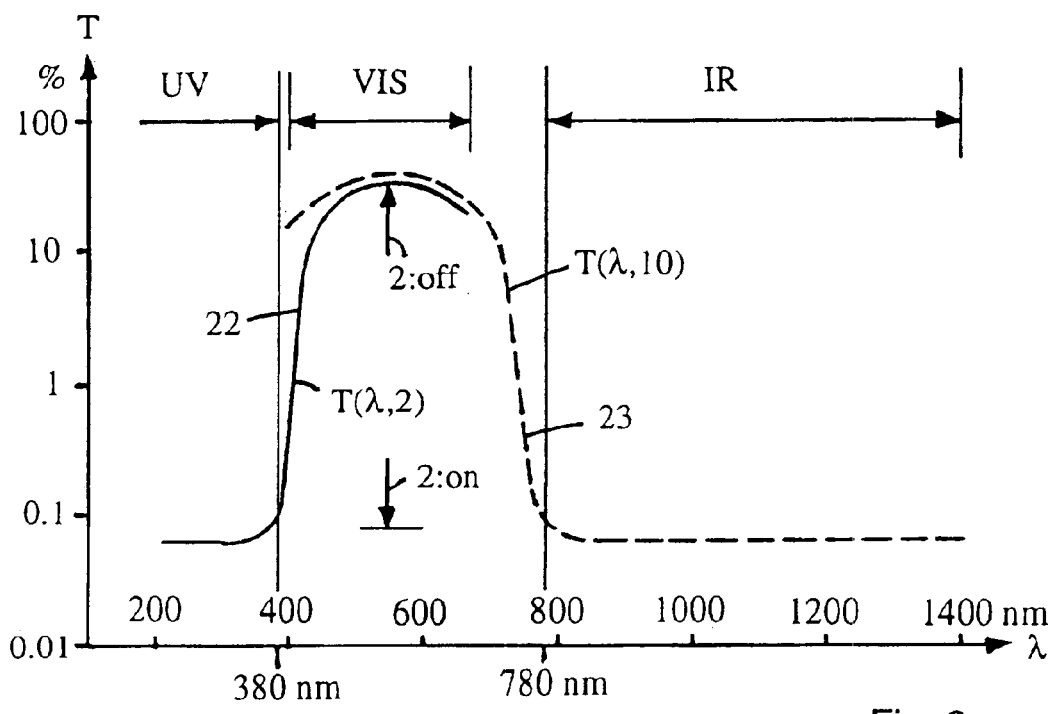
FIG. 2 illustrates spectral characteristics of the transmittance of the elements of a glare protection device according to the invention.

FIG. 2 depicts the spectral characteristic of the transmittance $T(\lambda)$ for the elements of the glare protection device: for the IR-plastic filter 10 and for the active electro-optical filter element 2 and with this their combined strong filtering effect in the UV-region (by 2) and in the IR region of the spectrum (by 10). The transmittance T here is logarithmically represented as a function of the wavelength λ. The curve 22 represents the transmittance characteristic T(λ, 2) of the active electro-optical filter element 2. As is manifest, the filter element's absorption in the UV region, e.g., from 200 nm, resp., 250 nm–380 nm is very high, with a transmittance of, preferably, at the maximum 0.1%, or, e.g., also only 0.0004%, depending on the required application of the glare protection device. In accordance with the eye protection regulations for welding applications according to the European Standard EN 169, version 2002, for example, for the protection scale number 13 at 380 nm a transmittance of only 0.00044% is prescribed. In the visible region of the spectrum VIS, e.g., from 400–650 nm, and in the non-activated condition (2: off), however, a relatively high transparency of, e.g., 5–15% is achieved, at least, however, of 3.2%.

UV absorption is preferably mainly achieved by the polarisation layers 8 and 18, which, for example, may contain corresponding triacetate.

The curve 23 illustrates the transmittance characteristic T(λ, 10) of the IR plastic filter 10, the absorption of which in the infrared region IR of 780–1400 nm is very high, with a transmittance of, for example, at maximum 0.1%. Depending on the required application and corresponding protection scale number of the glare protection device 1 in accordance with the European Standard EN 169, the transmittance value of the IR filter is able to be correspondingly adjusted, e.g., by the selection of the amount of dye and the thickness of the filter. Therefore, for example, for the required protection scale numbers 9, 10, 11, 12, a corresponding transmittance value in the IR region of the spectrum of 0.2%, 0.1%, 0.05% and 0.027% is capable of being produced.

As FIG. 2 illustrates, by means of a combination of the two layers 2 and 10, respectively, of their transmittance curves 22 and 23 in accordance with the invention, the required transmittance characteristic of the glare protection device 1 is capable of being produced over the whole spectrum from UV through the visible region VIS up to IR (from 200 up to 1400 nm).

Figure 3:
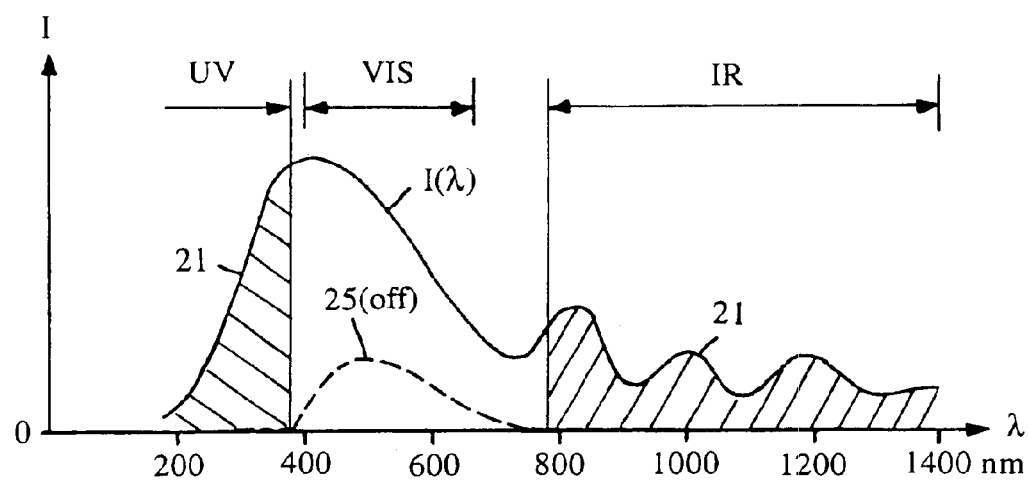
FIG. 3 an example of the spectral intensity characteristic of a welding light and of light emerging towards the observer.

FIG. 3 illustrates an example of a spectral intensity distribution I(λ) for a welding light 21, which impinges on the glare protection device 1. With the combination according to the invention of the elements: active electro-optical filter element 2 and stuck-on IR plastic filter 10, a spectral intensity distribution of the light passing through in accordance with curve 25 (in the non-activated condition of 2: off) is achieved with a relatively high transmittance solely in the visible range VIS of the spectrum.

Figure 4:
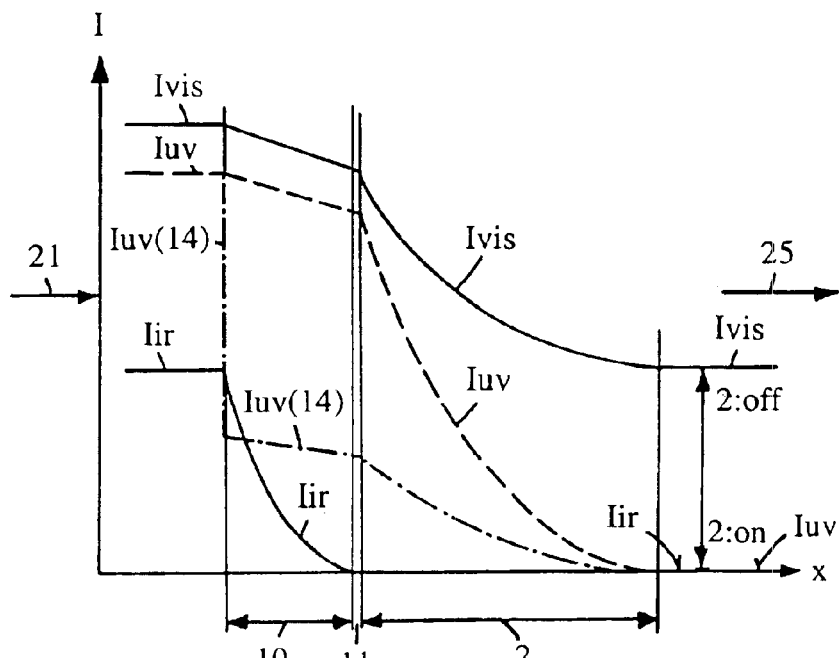
FIG. 4 shows the intensity characteristics of UV proportion, IR proportion, and visible light through the glare protection device.

FIG. 4 illustrates the absorption characteristic of UV and IR light during the passage of the entering welding light 21 through the layers of the IR plastic filter 10 and active electro-optical filter. For this purpose, the intensity characteristics I(x) for the UV region: Iuv, for the visible region VIS: Ivis and for the IR region of the spectrum: Iir are represented. As FIG. 4 illustrates, the UV intensity drops strongly in the active electro-optical filter 2 (absorption), while the IR intensity Iir drops strongly in the IR-plastic filter 10 and the visible light Ivis is reduced moderately in the electro-optical layer 2 and in the IR plastic filter. Accordingly, the light passing through 25 still contains a relatively high (as high as possible) proportion Ivis (in the non-activated condition 2: off).

As a further advantageous variant of the glare protection device according to the invention, for example, for applications with particularly high impinging UV radiation, the IR plastic filter 2 may comprise a further surface coating as a UV partly reflecting coating 14. A reflecting coating of this kind is significantly easier and at lower cost to manufacture (i.e., by dip coating) than the expensive glass reflecting filters up until now, because here only a coarse reduction of the UV intensity by a small factor, e.g., to 10–30%, is to be achieved, while subsequently the reduction of the UV light in the active filter element 2 takes place by magnitudes up to the required very low transmittance values (0.1%), as is illustrated with the curve Iuv (14). With this, also a possible high loading by the high UV radiation both of the IR dye as well as of the LCD cell would be reduced, if so required.

The IR plastic filter 10, depending on the application, may be arranged in front of, i.e., on the side of the welding light, behind, i.e., towards the observer, or also between two LCD elements in the active filter element 2 (if at least two LCD elements are present). The arrangement in front of the active filter element results in an additional mechanical protection, while with the arrangement behind the active filter element 2 the UV radiation has already been absorbed by the active filter element and as a result the dye of the IR plastic filter would not anymore be subjected to the high-energy UV radiation, which could further increase the lifetime of the dye.

For increasing the resistance against scratches, the IR filter 10 may also comprise a hard material coating 13 on its outside surface (e.g., of silicon oxide).

The IR plastic filter 10 consists of an optically pure, as stable as possible plastic material with an integrated, i.e., introduced into the plastic mass dye, which is also as stable over time as possible and is resistant with respect to the application conditions, e.g., heat-resistant up to at least 80° C. For example, it may contain a dyed in the mass monomer methyl-acrylate (MMA). Usable as plastic materials are also optically pure acrylic resins or polycarbonates and, for special applications, temperature-stable, heat-resistant plastic materials, such as, e.g., polyethersulphone (PES) or polymethyl-pentene (PMP).

Particularly simple and cheap production method for the IR plastic fitter (10) are extruding, molding or compression molding. These production methods replace the very elaborate and expensive deposition of very many thin coats in a high vacuum required to form the reflective layers of the filters up until now.

The glare protection 1 device in accordance with the invention advantageously may form an assembly together with the filter module and the electronics, i.e., a cartridge, which is capable of being installed, resp., inserted for any application required.

Figure 5:
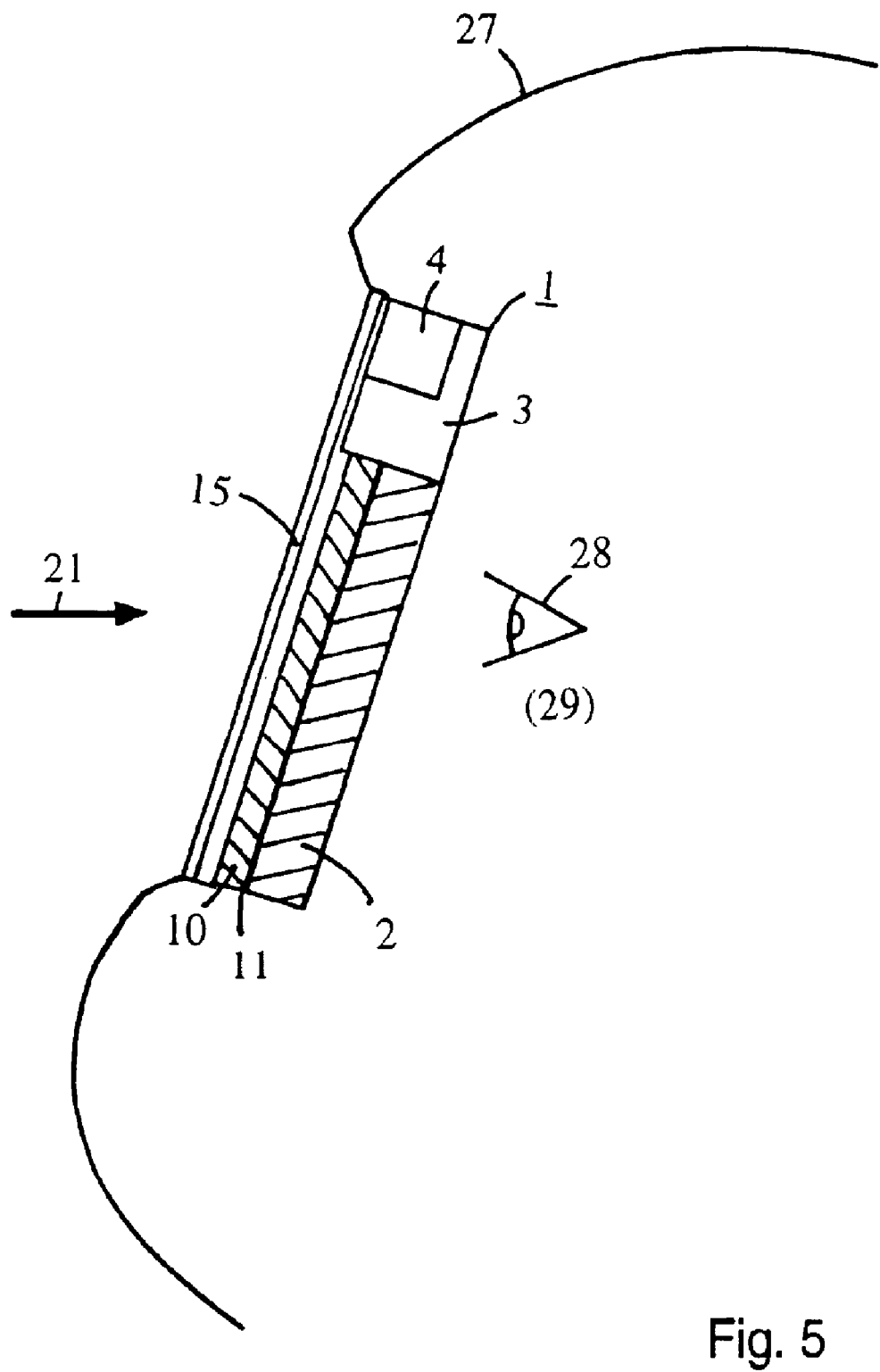
FIG. 5 shows a glare protection device in a welding protective mask.

FIG. 5 as an example depicting a cartridge of this kind, which is built into a welding protective mask 27 as a sight window. This illustrated cartridge and glare protection device 1 consists of an active electro-optical filter element 2, an IR plastic filter 10, an electronic control circuit 3 for the active filter element, and a signal transmitter 4 for controlling the electronic control circuit 3 and with it the active filter element. In most cases, this signal transmitter 4 consists of an optical detector, which senses the welding light. In other applications, it may also be driven by the control system of a complete welding installation.

An interchangeable protective sheet 15, e.g., made out of polycarbonate, as a cheap consumable component, serves as an impact protection and as a protection against welding splatter.

Thus the glare protection device 1 as a cartridge, e.g., is also capable of being utilised for the observation of welding points by means of a video camera 29 in welding robots (FIG. 1), wherein here the signal transmitter 4 could also be driven by the control system of the welding robot.

As a further application, a cartridge of this type may also be installed at suitable points as a sight window for observing a glass- or metal melt bath.

Within the scope of this application, the following terms are utilised:

1 Glare protection device, cartridge;
2 Active electro-optical filter element;
3 Electronic control circuit;
4 Signal transmitter;
5 LCD-layer;
6, 16 Electrodes;
7, 17 Glass plates;
8, 18 Polarisation layers;
10 IR-plastic filter;
11 Adhesive layer;
13 Hard material coating;
14 UV-partly reflecting coating;
15 Protective sheet;
21 Welding light, entering radiation;
22 Transmittance of 2, T($\lambda$);
23 Transmittance of 10, T($\lambda$);
25 Emerging radiation;
27 Welding protective mask;
28 Observer;
29 Video camera;
T Transmittance;
I Light intensity;
$\lambda$ Wavelength;
UV UV region of the spectrum;
IR IR region of the spectrum;
VIS visible region of the spectrum;
Iuv, Ivis, Iir intensities of UV, VIS, IR;

What is claimed is:

1. A glare protection device comprising:
an active electro-optical filter element (2), which comprises at least one liquid crystal (LCD) layer (5) as well as polarisation layers (8, 18), with a dedicated electronic control circuit (3) for controlling the transmission of the active electro-optical filter element (2), wherein the active electro-optical filter element (2) practically completely absorbs the ultraviolet (UV) radiation in the spectrum up to 380 nm so that the UV-transmittance of the active electro-optical filter element (2) in the spectrum up to 380 nm amounts to a maximum of about 0.1%, and wherein the UV-absorption takes place primarily in the polarisation layers (8, 18) of the active electro-optical filter element (2);
an infrared (IR) plastic filter (10) comprising a dye that is stable over time, and that absorbs infrared (IR) radiation in a wavelength range of at least 780 nm to 1400 nm, wherein the IR-plastic filter (10) is completely joined to the active electro-optical filter element (2) by means of a compact adhesive layer (11); and
the IR-plastic filter (10) and the active electro-optical filter element (2) together form a compact optical and mechanical unit (1) having a transmittance in the visible range of the spectrum from 400 nm to 650 nm, which amounts to at least 3.2%.

2. The glare protection device according to claim 1, wherein transmittance of the IR-plastic filter (10) between 780 and 1400 nm amounts to a maximum of 0.1%.

3. The glare protection device according to claim 1, wherein the IR-plastic filter (10) has a thickness of between 0.5 and 1.5 mm.

4. The glare protection device according to claim 1, wherein the IR-plastic filter (10) consists of a temperature-stable, heat-resistant, optically pure polymer.

5. The glare protection device according to claim 1, wherein the IR-plastic filter is formed from at least one of polyether-sulphone (PES) and polymethyl-pentene (PMP).

6. The glare protection device according to claim 1, wherein the IR-plastic filter (10) is manufactured by one of extruding, moulding, and compression moulding.

7. The glare protection device according to claim 1, wherein a ratio of an average line absorption coefficient of the dye in the IR plastic filter (10) in the IR-region of the spectrum (780–1400 nm) to that in the visible region of the spectrum (VIS) is at least 5:1.

8. The glare protection device according to claim 1, wherein the adhesive layer (11) is selected from the group consisting of: epoxy, light-hardening epoxy, and silicone resin.

9. The glare protection device according to claim 1, wherein a refraction index of the adhesive layer (11) is adapted to a refraction index of the IR-plastic filter (10) and the polarisation layer (8).

10. The glare protection device according to claim 1, wherein the IR-plastic filter comprises an external coating of hard material (13).

11. The glare protection device according to claim 1, wherein the IR-plastic filter (10) comprises an additional UV-reflecting coating (14).

12. The glare protection device according to claim 1, wherein the IR-plastic filter (10) is arranged on a side of the welding light that is facing toward an observer or between two LCD-elements in the active protection filter (2).

13. The glare protection device according to claim 1, wherein said device is built into a welding protective mask (27) as a sight window.

14. The glare protection device in accordance with claim 1, wherein said device is installed on an automatic welding machine in front of a video camera (29) or as an observation window.

15. The glare protection device according to claim 1, wherein said device is arranged as a sight window for the observation of a glass- or metal melt.

16. A glare protection device comprising:
an active electro-optical filter element (2), which comprises at least one liquid crystal (LCD) layer (5) as well as polarisation layers (8, 18), with a dedicated electronic control circuit (3) for controlling the transmission of the active electro-optical filter element (2), wherein the active electro-optical filter element (2) practically completely absorbs the ultraviolet (UV) radiation in the spectrum up to 380 nm so that the UV-transmittance of the polarisation layers (8, 18) of the active electro-optical filter element (2) in the spectrum up to 380 nm amounts to a maximum of about 0.1%;
an infrared (IR) plastic filter (10) comprising a dye that is stable over time, and that absorbs infrared (IR) radiation in a wavelength range of at least 780 $\mu$m to 1400 $\mu$m, so that the mean transmittance of the IR-plastic filter (10) between 780 nm and 1400 nm amounts to a maximum of 0.2%, wherein the IR-plastic filter (10) is completely joined to the active electro-optical filter element (2) by means of a compact adhesive layer (11); and the IR-plastic filter (10) and the electro-optical active filter element (2) together form a compact optical and mechanical unit (I) having a transmittance in the visible range of the spectrum from 400 nm to 650 nm, which amounts to at least 3.2%.

* * * * *

UNITED STATES PATENT AND TRADEMARK OFFICE
CERTIFICATE OF CORRECTION

PATENT NO. : 6,887,531 B2  Page 1 of 1
DATED : May 3, 2005
INVENTOR(S) : Hones

It is certified that error appears in the above-identified patent and that said Letters Patent is hereby corrected as shown below:

Column 6,
Lines 64 and 65, delete "$\mu$m" and insert -- nm --.

Signed and Sealed this

Twenty-third Day of August, 2005

JON W. DUDAS
*Director of the United States Patent and Trademark Office*